United States Patent [19]

Teeter

[11] 4,054,142
[45] Oct. 18, 1977

[54] METHOD FOR ATTACHING A PORTABLE URINARY SYSTEM

[76] Inventor: Dorothy M. Teeter, P.O. Box 362, Bryant, Ark.

[21] Appl. No.: 643,192

[22] Filed: Dec. 22, 1975

[51] Int. Cl.² .............................................. A61F 5/44
[52] U.S. Cl. .................................... 128/295; 128/157
[58] Field of Search ............... 128/294, 295, 386, 157, 128/2 F, 138 R

[56] References Cited

U.S. PATENT DOCUMENTS

| 3,511,241 | 5/1970 | Lee | 128/295 |
|---|---|---|---|
| 3,661,155 | 5/1972 | Lindan | 128/295 |
| 3,742,953 | 7/1973 | Lee | 128/295 |
| 3,835,857 | 9/1974 | Rogers et al. | 128/295 |

*Primary Examiner*—Dalton L. Truluck
*Assistant Examiner*—Henry S. Layton

*Attorney, Agent, or Firm*—Huebner & Worrel

[57] ABSTRACT

An improved method for attaching to the external urinary organ of a male patient a portable urinary system characterized by a urinal bag adapted to be attached to the patient's leg, a rubber sheath for receiving the patient's urinary organ, and a flexible conduit extended between the sheath and the bag including the steps of inserting a patient's organ into a rubber sheath connectable to a flexible conduit, applying to the external surface of the sheath at least one circumscribing layer of surgical dressing, applying to the layer of surgical dressing a circumscribing nonadhesive elastic band and releasably connecting the opposite ends of the band employing a Velcro fastener, connecting the urinal bag to the patient's leg employing a pair of elastomeric bands and connecting the conduit between the sheath and the bag.

1 Claim, 4 Drawing Figures

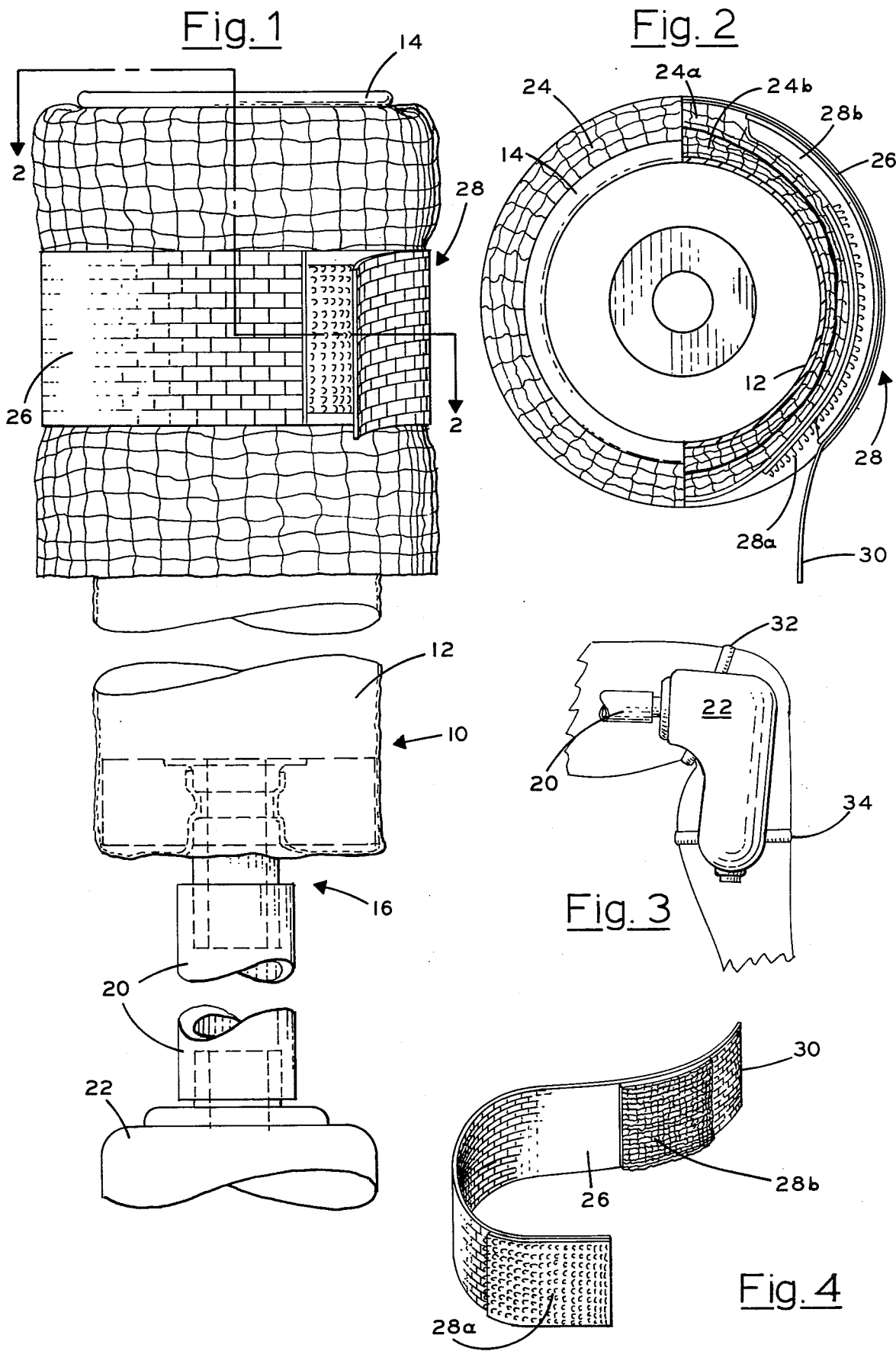

METHOD FOR ATTACHING A PORTABLE URINARY SYSTEM

BACKGROUND OF THE INVENTION

1. Field of the Invention

The invention generally relates to a technique for attaching to a male patient suffering from urinary incontinence a portable urinary system characterized by a urinal bag adapted to be attached to the patient's leg, a rubber sheath for receiving the patient's urinary organ, or penis, and a flexible conduit extended between the sheath and the bag, and more particularly to an improved method for attaching the sheath of such a system to the external urinary organ of a male patient.

As can fully be appreciated by those familiar with the care of male patients suffering from urinary incontinence, a great deal of attention must be paid to the collection of urine inadvertently discharged from the patient for obvious aesthetic and clinical reasons. As can also be appreciated, a myriad of problems confront users of systems currently employed in collecting urine from such patients. The magnitude of the problems faced is much greater, of course, for patients having additional disabilities such as loss of motor control for various limbs.

2. Description of the Prior Art

Presently, in providing for the collection of urine, it is common practice to attach to patients portable urinary systems characterized by urinal bags adapted to be attached to the patient's legs and receivers for the external urinary organs of the patients. From the receiver there is extended a flexible conduit adapted to be connected with the bag. Several types of portable urinary systems currently are available for use by male patients. However, in each instance, the system is characterized by a receiver comprising a rubber sheath configured to receive the patient's external urinary organ.

It has, heretofore, been common practice to secure such a sheath in place simply by applying an elastic adhesive-bearing tape about the surface of the sheath. Unfortunately, elastic tape applied directly to a rubber sheath does not readily provide for adjustment since the tape cannot be released and reapplied. As a consequence, should tape be applied too tightly or too loosely, the sheath must be removed and replaced. The inherent inadequacy of the prior art techniques often results in a loss of time as well as accidental spillage. Moreover, a patient having debilitated tactile senses in the lower portion of his body may not be able to detect the presence or absence of the sheath and/or other conditions, such as swelling, of the urinary organ.

Consequently, where the patient must be transferred employing lifts, hoists and the like, it is possible for the patient to lose a sheath without being aware of its absence. Similarly, where the sheath is taped in place with sufficient tension for thus assuring that dislocation of the sheath will not occur during patient handling operations, the organ may experience swelling as a result of the tape being applied too tightly. Of course, where swelling occurs, it can be alleviated only by releasing the tape.

Another disadvantage often encountered in employing a rubber sheath as a receptacle for a male patient's external urinary organ is that of inducing inflamation and lesions in the patient's skin, particularly in the more sensitive areas.

Finally, the method heretofore employed in equipping a patient with a portable urinary system normally requires that the bag be strapped to the patient's leg utilizing straps formed of rubber materials having the ends thereof interconnected employing buttons received within buttonholes. Such bottons are particularly difficult for a patient to manipulate with the result that often a slit is made in the straps to weaken the area around the buttonholes with the result that the strap tends to rupture in the vicinity of the buttonhole when placed in use.

It should, therefore, be apparent that there currently exists a need for an improved method of attaching existing portable urinary systems to male patients which facilitates rapid attachment, detachment and adjustment in order to overcome the aforementioned difficulties and disadvantages.

It is, therefore, the general purpose of the instant invention to provide a reliable, practical and improved method for attaching to the urinary organs of male patients a portable urinary system regardless of differences in anatomic size resulting from stages of maturity and/or stimuli, which method facilitates a rapid positioning and repositioning of a sheath, and an attachment of the urinal bag while avoiding a skin disorders frequently induced through a use of a rubber sheath.

OBJECTS AND SUMMARY OF THE INVENTION

It is, therefore, an object of the instant invention to provide an improved method for attaching to a male patient a portable urinary system which overcomes the aforementioned difficulties and disadvantages.

It is another object to provide an improved method for attaching a receiver for a portable urinary system to the external urinary organ of a male patient.

It is another object to provide an improved method for attaching a sheath to the external urinary organ of a male patient which accommodates subsequent adjustment and readjustment of the sheath.

It is another object to provide an improved method for attaching to the penis of a male patient suffering from urinary incontinence a rubber sheath without inducing epidermal irritation.

These and other objects and advantages are achieved by inserting a male patient's urinary organ into a rubber sheath, applying to the external surface of the sheath at least one circumscribing layer of surgical dressing, but preferably two layers formed by folding a gauze pad into superimposed layers, applying about the thus formed cylindrical layer of surgical dressing an elastomeric band of woven fabric having the opposite halves of a Velcro fastener attached thereto at the opposite ends thereof, uniting the opposite end of the band by interconnecting the Velcro fastener, and thereafter attaching the urinal bag to the patient's leg by securing the bag thereto using a pair of elastomeric bands of woven fabric having opposite halves of Velcro fasteners attached thereto at the opposite ends thereof, as will become more readily apparent by reference to the following description and claims in light of the accompanying drawings.

BRIEF DESCRIPTION OF THE DRAWINGS

FIG. 1 is a fragmented view of a portable urinary system, depicting the manner in which the sheath thereof is secured employing the method of the instant invention.

FIG. 2 is a partially sectioned view, taken generally along line 2—2 of FIG. 1.

FIG. 3 is a fragmented view depicting a urinal bag attached to a patient's leg employing the method of the instant invention.

FIG. 4 is a perspective view of an elastomeric band of woven fabric employed in attaching the sheath and the urinal bag in accordance with the principles of the instant invention.

DESCRIPTION OF THE PREFERRED EMBODIMENT

Referring now to the drawings wherein like reference characters designate like or corresponding parts throughout the several views, there is shown in FIG. 1 a sheath, generally designated 10, in a configuration duplicating the configuration normally assumed when attached to the external urinary organ of a male patient, not shown.

The sheath 10, as illustrated, is typified by a commercially available sheath sold under the trademark Uro-Don. While the specific sheath employed is of little significance, it should be apparent that it includes a cylindrical body 12 formed of a thin rubber membrane having provided at its base an annular rib 14. A fluid coupling 16 is connected to the sheath at its distal end. The fluid coupling 16, also of little significance, includes a tubular stem 18 suitably connected in sealing relationship with the body 12. The stem 18 serves, in turn, to receive a tubular conduit 20 which is employed to connect the sheath 10 with a urinal bag 22. The urinal bag 22, like the sheath 10, is well known, therefore a detailed description of the urinal bag is omitted in the interest of brevity. However, it is to be understood that the sheath 10, tubular conduit 20, and urinal bag 22 form a portable urinary system particularly suited for collecting urine inadvertently discharged by male patients suffering from urinary incontinence.

Once a urinary organ is seated in the sheath 10, a pressure distribution pad 24 is applied to the sheath in an encircling relationship with the external surface thereof, adjacent the annular rib 14. As a practical matter, the pressure distribution pad 24 is formed by folding a 4 × 4—12 ply gauze pad along its center line to thus form a pair of superimposed layers, designated 24a and 24b.

About the outer surface of the pressure distribution pad 24 there is applied, in circumscribing relationship therewith, an elastomeric band 26 of woven fabric material. Such material frequently is employed in the garment industry and is commercially available under the generic name "elastic". Such elastic is characterized by fabric coated elastomeric materials interwoven with fabric threads.

The opposite ends of the bands 26 are releasably united by a commercially available Velcro fastener designated 28. The Velcro fastener, as shown, is characterized by a hook plate 28a and wool plate 28b. These plates are stitched to the opposite end portions of the band 28 to be employed in a manner well understood.

In applying the band 26 to the pressure distribution pad 24, the hook plate 28a is faced outwardly so that the wool plate 28b can be forced inwardly, with respect to the sheath, in order to facilitate a rapid union between the opposite halves of the Velcro fastener. In practice, the band 26 extends beyond the wool plate 28b and provides a tab, designated 30, which can readily be grasped and tensioned by the patient, or an attendant, for purposes of separating the plates 28a and 28b in a manner well understood by those familiar with Velcro fasteners.

It should, of course, be apparent that the length of the band 26 is sufficient to make a single pass about the pressure distribution pad 24, while the plates 28a and 28b are of a length sufficient to permit the end portions of the band to be joined at different locations for accommodating an adjustment of the tightness of the band 26. Hence, the sheath is releasably secured in place in a manner such that pressure is substantially evenly distributed and the likelihood of irritation of the patient's skin is reduced.

Once the sheath 10 has been applied in the manner hereinbefore described, the urinal bag 22 is mounted on the patient's leg employing a pair of elastomeric bands 32 and 34, each preferably having attached to its opposite ends the opposed plates of a Velcro fastener, not shown. However, it is to be understood that the bands 32 and 34 are similar in design and material to the band 26, differing only in the length thereof which permits the bands to be passed about the patient's leg, not designated, and secured in place by joining the opposite halves, or plates, of the Velcro fastener 28.

The tubular conduit 20 is now connected with the sheath 10 and the urinal bag 22 in a manner well understood by those familiar with such devices.

When employing the method which embodies the principles of the instant invention, a portable urinary system can be attached to a male patient by himself, where practicable, or by his attendant. For example, once a patient has been bathed in a suitable basin and thereafter toweled-off, a portable urinary system is attached to the patient, employing the method. Once the system has been applied, a lift is utilized in returning the patient to his bed. Since the band 26 can be applied relatively tightly, handling of the patient is facilitated, without apprehension. The patient upon being returned to a rest configuration, in his bed, or other suitable location, is again examined. Where the band is found to be too light the tab 30 of the band 26 is lifted by the patient, or an attendant, for separating the halves of the Velcro fastener, otherwise herein referred to as the hook plate 28a and the wool plate 28b. Thus tension is relieved in the band. By relieving the tension, swelling of the urinary organ is avoided. Furthermore, due to the large surface area of the pressure distribution pad, as well as the cushioning effect of the pad, against the outer surface of the sheath 10, the tendency to develop inflamation and lesions of the epidermal layers is greatly reduced.

Thus, in practice, the method which embodies the principles of the instant invention facilitates a safe and practical attachment, to the external urinary organ of a male patient, of a portable urinary system characterized by a urinal bag adapted to be attached to the patient's leg, a rubber sheath for receiving the urinary organ, and a flexible conduit extended between the sheath and the bag, without subjecting the patient to undesirable effects heretofore experienced when utilizing techniques which require the sheath to be secured in place using adhesive coated elastic tape applied directly to the surface of the sheath.

Although the invention has been shown and described in what is conceived to be the most practical and preferred method, it is recognized that departures may be made therefrom within the scope of the invention, which is not to be limited to the illustrative details disclosed.

Having described my invention, what I claim as new and desire to secure by Letters Patent is:

1. In an improved method for attaching to an external urinary organ of a male patient a urinary incontinence device characterized by a reservoir comprising a urinal bag adapted to be attached to the patient's leg, and a flexible receiver for the patient's urinary organ comprising a thin rubber sheath, and a flexible conduit extended between the receiver and the reservoir, the steps comprising:
   A. inserting the patient's urinary organ into the sheath;
   B. folding in half a 4 × 4 12 ply gauze pad and applying the folded pad to the external surface of the sheath in an overlapping and circumscribing relation therewith for thus forming a pressure distribution pad near the base of the organ comprising multiple overlapping layers of surgical gauze;
   C. applying to the pressure distribution pad, in a circumscribing relationship therewith a nonadhesive elastomeric band of woven fabric having opposite halves of a Velcro fastener attached thereto at the opposite ends thereof; and
   D. releasably uniting the opposite end portions of said band by joining the opposite halves of the Velcro fasteners.

* * * * *